(12) United States Patent
Ertl et al.

(10) Patent No.: US 11,547,538 B2
(45) Date of Patent: Jan. 10, 2023

(54) METHOD AND ARRANGEMENT FOR CLEANING OF A CANAL

(71) Applicant: DENTSPLY SIRONA Inc., York, PA (US)

(72) Inventors: Thomas Ertl, Ranstadt (DE); Rolf Diebolder, Ulm (DE)

(73) Assignee: DENTSPLY SIRONA INC., York, PA (US)

( * ) Notice: Subject to any disclaimer, the term of this patent is extended or adjusted under 35 U.S.C. 154(b) by 0 days.

(21) Appl. No.: 15/465,746

(22) Filed: Mar. 22, 2017

(65) Prior Publication Data

US 2017/0274220 A1 Sep. 28, 2017

(30) Foreign Application Priority Data

Mar. 22, 2016 (DE) .................................. 16161539.8
Aug. 19, 2016 (DE) .................................. 16184968.2

(51) Int. Cl.
*A61C 5/50* (2017.01)
*A61C 17/02* (2006.01)
(Continued)

(52) U.S. Cl.
CPC .............. *A61C 17/02* (2013.01); *A61B 18/22* (2013.01); *A61C 1/0046* (2013.01); *A61C 5/50* (2017.02);
(Continued)

(58) Field of Classification Search
CPC .... A61N 5/0603; A61N 5/0624; A61N 5/062; A61N 5/067; A61N 2005/0606; A61N 2005/063; A61N 2005/0659; A61N 2005/0662; A61C 5/50; A61C 17/02; A61C 1/0046; A61C 19/003; A61B 18/22; A61B 2018/0063
See application file for complete search history.

(56) References Cited

U.S. PATENT DOCUMENTS 3,753,434 A    8/1973   Pike
4,480,996 A   11/1984   Crovatto
(Continued)

FOREIGN PATENT DOCUMENTS

CA     2020712 A1    1/1991
CN     1278157 A    12/2000
(Continued)

OTHER PUBLICATIONS

International Search Report; PCT/EP2017/056751; dated Sep. 4, 2017 (completed); Sep. 20, 2017 (mailed).
(Continued)

*Primary Examiner* — Yogesh P Patel
(74) *Attorney, Agent, or Firm* — Dentsply Sirona Inc.

(57) ABSTRACT

The invention relates to a method and an arrangement for the cleaning of a circumferentially closed canal by means of a light guide conducting a laser beam. The entry of the laser beam into the light guide is interrupted when the free end of the light guide is outside of the canal and/or the movement of the light guide within the canal is monitored and that if there is no movement or the movement is below a threshold value then a signal is triggered and/or the laser radiation is turned off or its output is reduced.

13 Claims, 8 Drawing Sheets

(51) Int. Cl.
*A61C 5/55* (2017.01)
*A61C 1/00* (2006.01)
*A61N 5/06* (2006.01)
*A61B 18/22* (2006.01)
*A61C 13/15* (2006.01)
*A61N 5/067* (2006.01)
*A61B 18/00* (2006.01)

(52) U.S. Cl.
CPC .............. *A61C 5/55* (2017.02); *A61C 19/003* (2013.01); *A61N 5/062* (2013.01); *A61N 5/0603* (2013.01); *A61N 5/0624* (2013.01); *A61B 2018/0063* (2013.01); *A61N 5/067* (2021.08); *A61N 2005/063* (2013.01); *A61N 2005/0606* (2013.01); *A61N 2005/0659* (2013.01); *A61N 2005/0662* (2013.01)

(56) References Cited

U.S. PATENT DOCUMENTS

| | | | |
|---|---|---|---|
| 5,051,093 A | 9/1991 | Fitzmorris | |
| 5,092,773 A | 3/1992 | Levy | |
| 5,165,893 A | 11/1992 | Thompson | |
| 5,207,576 A | 5/1993 | Vassiliadis | |
| 5,415,652 A | 5/1995 | Mueller | |
| 5,846,080 A | 12/1998 | Schneider | |
| 6,162,052 A * | 12/2000 | Kokubu | A61B 18/22 433/29 |
| 7,306,459 B1 | 12/2007 | Williams | |
| 7,942,915 B2 | 5/2011 | Altshuler | |
| 7,942,916 B2 * | 5/2011 | Altshuler | A61B 18/203 607/88 |
| 8,388,340 B2 * | 3/2013 | Crohn | A61C 19/041 433/72 |
| 9,119,548 B2 | 9/2015 | Just | |
| 2002/0115991 A1 | 8/2002 | Edwards | |
| 2003/0124482 A1 | 7/2003 | Calvert | |
| 2004/0224288 A1 * | 11/2004 | Bornstein | A61C 5/50 433/29 |
| 2006/0140531 A1 * | 6/2006 | Shin | G01B 11/18 385/12 |
| 2007/0072153 A1 | 3/2007 | Gross | |
| 2008/0021441 A1 | 1/2008 | Altshuler | |
| 2008/0219629 A1 | 9/2008 | Rizoiu | |
| 2008/0285017 A1 | 11/2008 | Mitchell | |
| 2009/0130622 A1 * | 5/2009 | Bollinger | A61C 1/0046 433/29 |
| 2009/0220908 A1 | 9/2009 | Glover | |
| 2009/0220909 A1 | 9/2009 | Mueller | |
| 2009/0221931 A1 * | 9/2009 | Crohn | A61C 19/041 600/547 |
| 2010/0239996 A1 * | 9/2010 | Ertl | A61B 90/06 433/29 |
| 2010/0330523 A1 * | 12/2010 | Kert | A61N 5/062 433/29 |
| 2010/0330539 A1 | 12/2010 | Glover | |
| 2011/0217665 A1 | 9/2011 | Walsh | |
| 2011/0270241 A1 | 11/2011 | Boutoussov | |
| 2012/0123399 A1 * | 5/2012 | Belikov | A61B 18/201 606/16 |
| 2012/0237893 A1 * | 9/2012 | Bergheim | A61C 5/44 433/81 |
| 2012/0264078 A1 * | 10/2012 | Patel | A61N 5/0624 433/29 |
| 2013/0040267 A1 * | 2/2013 | Bergheim | A61C 3/03 433/216 |
| 2013/0310862 A1 | 11/2013 | Seto | |
| 2013/0323673 A1 | 12/2013 | Hakomori | |
| 2013/0325003 A1 | 12/2013 | Kapur | |
| 2014/0017636 A1 | 1/2014 | Berger | |
| 2014/0087333 A1 | 3/2014 | Divito | |
| 2014/0088488 A1 | 3/2014 | Loeb | |
| 2014/0100560 A1 | 4/2014 | Biadillah | |
| 2014/0335475 A1 | 11/2014 | Berger | |
| 2015/0010882 A1 * | 1/2015 | Bergheim | A61C 17/02 433/80 |
| 2015/0086941 A1 * | 3/2015 | Katsuda | A61C 5/48 433/102 |
| 2015/0147718 A1 * | 5/2015 | Khakpour | A61C 17/0202 433/81 |
| 2015/0173852 A1 | 6/2015 | Khakpour | |
| 2015/0230900 A1 | 8/2015 | Gente | |
| 2015/0230902 A1 * | 8/2015 | Andreou | A61C 5/42 433/27 |
| 2015/0283402 A1 | 10/2015 | Grenon | |
| 2015/0374454 A1 | 12/2015 | Beerstecher | |
| 2016/0067149 A1 * | 3/2016 | Kishen | A61K 6/20 433/224 |
| 2016/0287364 A1 * | 10/2016 | Pauler | A61B 1/24 |
| 2018/0177564 A1 * | 6/2018 | Boutoussov | A61C 1/0015 |

FOREIGN PATENT DOCUMENTS

| | | |
|---|---|---|
| CN | 1359278 A | 7/2002 |
| CN | 101060816 A | 10/2007 |
| CN | 201578386 U | 9/2010 |
| CN | 102596270 A | 7/2012 |
| EP | 0487435 A2 | 5/1992 |
| EP | 0780097 A2 | 6/1997 |
| EP | 1711849 A2 | 10/2006 |
| GB | 201304125 | 4/2013 |
| JP | 2003525072 A | 8/2003 |
| JP | 2014004329 A | 1/2014 |
| KR | 20020012591 A | 2/2002 |
| RU | 2443396 C1 | 2/2012 |
| RU | 2543031 C1 | 2/2015 |
| WO | 0074587 A1 | 12/2000 |
| WO | 2005070153 A2 | 8/2005 |
| WO | 2009064947 A1 | 5/2009 |
| WO | 2010145802 A1 | 12/2010 |
| WO | 2013049832 A2 | 4/2013 |
| WO | 2016036579 A1 | 3/2016 |

OTHER PUBLICATIONS

Written Opinion of the International Searching Authority; PCT/EP2017/056751; dated Sep. 4, 2017 (completed); Sep. 20, 2017 (mailed).

International Preliminary Report on Patentability; PCT/EP2017/056751; dated May 14, 2018 (completed); Jan. 17, 2018 Date of submission of the demand).

"Thermal and acoustic problems on root canal treatment with different lasers"; SPIE vol. 2327; Medical Applications of Lasers II (Dec. 23, 1994); T. Ertl, H. Benthin& G. Muller.

"Application of lasers in endodontics"; SPIE vol. 3192; Medical Applications of Laser in Dermatology, Ophthalmology, Dentistry and Endoscopy (Dec. 22, 1997); T. Ertl, H. Benthin, B. Jajaron & G. Mueller.

"Canal Enlargement by Er: YAG Laser Using a Cone-Shaped Irradiation Tip"; J Endodontics vol. 26, No. 8; Aug. 2000; pp. 454-458; S. Shoji, H. Hariu & H. Horiuchi.

"Effectiveness of the Erbium: YAG laser and new design radial and stripped tips in removing the smear layer after root canal instrumentation"; Lasers Med Sci (Mar. 27, 2012); pp. 273-280; E. DiVito, O.A. Peters &G. Olivi.

South Korean Office Action dated Jan. 11, 2021.
Chinese Office Action dated Dec. 16, 2020.
Brazilian Office Action dated Apr. 8, 2021.

* cited by examiner

METHOD AND ARRANGEMENT FOR CLEANING OF A CANAL

THE CROSS-REFERENCE TO RELATED APPLICATIONS

This patent application claims the benefit of and priority to European Patent Application No. 16184968.2, filed on Aug. 19, 2016 and European Patent Application No. 16161539.8, filed on Mar. 22, 2016, which are herein incorporated by reference for all purposes.

TECHNICAL FIELD

The invention relates to a method for the cleaning of a circumferentially closed canal by means of a light guide conducting a laser beam. The invention further relates to an arrangement comprising a laser radiation source, a light guide conducting a laser beam as well as a handpiece.

BACKGROUND OF THE INVENTION

Medical instruments are often in contact with body fluids during surgical or diagnostic procedures which always have the risk of contamination with bacteria and debris. Many instruments like endoscopes or surgical instruments have small working channels, which are used to transport fluids or e.g. laser fibers into the body of a patient and even worse body fluids are removed via these channels from the body of a patient.

Therefore, efficient sterilization procedures for those devices are important as long the devices are no disposables. Especially the working channels are problematic from a hygiene standpoint, as they are not easy accessible and not visible from outside.

Conventional cleaning is done by soaking in a cleaning fluid and/or flushing a cleaning fluid through the working canals. Typically no direct check is done whether the cleaning was successful.

SUMMARY OF THE INVENTION

An object of the present invention is it to provide a method and an arrangement for the cleaning of a circumferentially closed canal by means of laser beams. In connection with this, it has to be ensured on the one hand that the canal will not be damaged. On the other hand, it must also be ensured that persons are not put at risk by the laser beam. Another aspect of the invention is it to provide the possibility that the cleaning of the canal can be carried out in a simple manner wherein the procedure helps avoiding errors. Another aspect of the invention is to provide a compact unit by means of which the treatment as cleaning will be carried out.

The arrangement shall, in particular, enable its use without risking an incorrect treatment. It shall provide the possibility of an automated canal cleaning and canal treatment.

To solve one or more aspects, the invention provides a method for the cleaning of a circumferentially closed canal by means of a light guide conducting a laser beam, wherein the entry of the laser beam into the light guide is interrupted when the free end of the light guide is outside of the canal and/or the movement of the light guide within the canal is monitored and that if there is no movement or the movement is below a threshold value then a signal is triggered and/or the laser radiation is turned off or its output is reduced.

An independent proposal to solve the problem provides that the position of the free end of the light guide within the canal is checked and/or monitored.

According to a further independent proposal it is provided that a material present on the inside of the canal is removed through laser-induced hydrodynamic fluid movement.

According to a further independent proposal it is provided that a closure element is secured to one free end of a light guide conducting a laser beam, the light guide with the closure element is introduced into the canal, that the closure element is positioned in the region of the canal to be sealed and after positioning of the closure element energy is introduced, the closure element melts and/or softens and remains in this position in the canal and seals it tightly.

According to a further independent proposal it is provided that the closure element is melted through the laser radiation transmitted through the light guide or through electrical energy.

According to a further independent proposal it is provided that the closure element is connected to the free end of the light guide by means of a connecting material, with the melting temperature T1 thereof being higher than the melting temperature T2 of the closure element material.

According to a further independent proposal it is provided that after sealing of the canal, in particular its opening, a closure material is introduced into the canal and the light guide within the closure material is moved in the longitudinal axis direction of the canal at the same time as the laser beam is introduced.

According to a further independent proposal it is provided that mechanical effect of the energy introduced into the closure material via the laser radiation is greater than the macroscopic thermal effect of the energy introduced.

According to a further independent proposal it is provided that a sealing material is used that melts and/or foams through the introduction of heat energy and forms a closed-pore canal seal after cooling, in particular that sodium hydrogen carbonate enveloped by gutta percha material is used as the sealing material.

According to a further independent proposal it is provided that a material that comprises a first component and a second component which react with one another in a volume-expanding manner is used as sealing material.

According to a further independent proposal it is provided that a material is used as a closure element that comprises an in particular volume-scattering core material and an expanding material that envelops it.

According to a further independent proposal it is provided that an Er:YAG laser, Er:YSGG laser or CTE laser is used as the laser.

According to a further independent proposal it is provided that the laser is operated with a pulse duration between 5 µs and 1000 µs, preferably between 25 µs and 400 µs, and especially preferably between 50 µs and 200 µs.

According to a further proposal it is provided that a laser beam is used that has a pulse energy exiting from the light guide between 0.5 mJ and 50 mJ, in particular between 1 mJ and 10 mJ.

According to a further independent proposal it is provided that a verification of whether the light guide is inside the canal or outside the canal is carried out through
a) the radiation received by the light guide that is derived from the area surrounding the light guide, and/or
b) through the changing reflection component of the radiation reflected at the end of the light guide, and/or
c) measurement of a change in impedance via an outer metallization of the light guide.

According to a further independent proposal it is provided that the positioning of the light guide is verified redundantly, in particular by means of the steps a)+b) or a)+c) or b)+c), especially preferred by means of a)+b)+c).

Subject matter of the invention is also an arrangement comprising a laser radiation source, a light guide conducting a laser beam as well as a handpiece, wherein the handpiece is connected to a delivery device detachably and preferably rotationally, via which at least the laser beam and a liquid can be fed to the handpiece, as well as a first line guiding the liquid, that extends with its aperture side in the region of the light guide, and with the laser beam being directed into a canal via the light guide detachably connected with the handpiece.

A further proposal according to the invention provides that the handpiece is connected to at least one cleaning fluid container or has such a container, from which a line emanates, the opening of which extends on the light guide side.

A further proposal according to the invention provides that the cleaning fluid container is connected to the handpiece such that it can be detached or plugged on to it.

A further proposal according to the invention provides that the device has further exchangeable, disposable containers for different cleaning fluids (as sterile water and/or NaOCl and/or EDTA and/or PDT-fluids) which are pressurized by compressed air of a dental chair provided by a dental turbine connector.

A further proposal according to the invention provides that the cleaning fluid container is provided with a closable exit opening that can be controlled by an electromagnetically-actuatable valve controlled by a microcontroller.

A further proposal according to the invention provides that the electromagnetic valve is separated into an excitation part with a magnetic coil and a part of a ferromagnetic core in the hand piece and a ferromagnetic material as valve opener as part of the exit valve in a container.

A further proposal according to the invention provides that a flexible membrane or a piston separates the fluid from an air inlet.

A further proposal according to the invention provides that the light guide has a metallisation on its outer surface.

A further proposal according to the invention provides that the light guide has a metallisation on its outer surface with two regions that are electrically insulated with respect to one another.

A further proposal according to the invention provides that the regions insulated with respect to one another enmesh in one another in a comb-like manner at least at the tip of the light guide.

A further proposal according to the invention provides that the metallisation has hydrophobic characteristics over at least the anterior ⅓ of the light guide.

A further proposal according to the invention provides that a movement sensor is integrated into the handpiece.

A further proposal according to the invention provides that a movement sensor and a rotation encoder are integrated into the handpiece for recognition of the handpiece rotation with respect to a delivery system.

A further proposal according to the invention provides that the light guide between a delivery device and the handpiece is made of a material, in particular of GeO, sapphire or $ZrF_4$, which conducts laser pulses at least up to 50 mJ and/or a mean laser output of 5 W in the wavelength range preferably between 2.69 µm and 2.94 µm, as well as in particular additionally in the wavelength range between 400 nm and 1000 nm.

A further proposal according to the invention provides that the light guide to be introduced into the canal is made of a material, in particular of OH-reduced silica or sapphire, which conducts laser pulses at least up to 50 mJ and/or a mean laser output of 5 W in the wavelength range preferably between 2.69 µm and 2.94 µm, as well as in particular additionally in the wavelength range between 400 nm and 1000 nm.

A further proposal according to the invention provides that the diameter of the light-conducting core of the light guide lies between 150 µm and 600 µm, in particular between 118 µm and 250 µm, wherein the light guide preferably has a protective layer on its outer side.

A further proposal according to the invention provides that the light guide has an outer diameter between 200 µm and 300 µm and/or a length between 25 mm and 40 mm.

A further proposal according to the invention provides that the laser is a diode-pumped Er:YAG laser, Er:YSGG laser or CTE laser with, in particular, a pulse duration between 5 µs and 1000 µs, preferably in the range 25 µs to 400 µs, especially preferred 50 µs to 200 µs, and/or a pulse energy between 0.5 mJ and 50 mJ, in particular between 1 mJ and 10 mJ and/or a mean output between 0.5 W and 10 W, preferably between 1 W and 3 W, with a pulse repetition rate in the range 50 Hz to 2000 Hz, preferably 50 Hz to 800 Hz.

A further proposal according to the invention provides that the arrangement is provided with a control device with touchscreen, as well as a housing that encloses the laser, which is connected to a supply device, in particular a medical one, through which the arrangement can be supplied with water and/or compressed air.

Using a laser to generate steam bubbles and generating rapid fluid motion can improve the cleaning of small instrument canals significantly. Of course it is important not to damage the inner surface of the canals, which are often made of polymers and plastics. Therefore a laser with low pulse energy below the ablation threshold of the canal wall material is required. A diode pumped Er:YAG laser is ideal for this purpose, since the pulse repetition rate can be much higher than with conventional flashlamp pumped laser systems and can compensate for a lower pulse energy per pulse.

Killing bacteria in the working canals can be enhanced by using transient heat pulses as described in the text above Low power Er:YAG laser radiation in the order of 0.5 W with 200-800 Hz pulse repetition rate is fully sufficient to reach transient local peak temperatures on the canal wall well above 100° C. for killing bacteria and keeping the base temperature of canal wall material well below melting point or destruction thresholds.

It is important not to stay in one position with the cleaning fiber because this could cause local overheating of the sensitive canal walls. Therefore the motion detection of the fiber is an additional safety feature in this cleaning application.

For laser safety reasons it is further helpful to avoid laser emission before the cleaning fiber is introduced into the canal. Therefore a "fiber in canal detection" is provided with details described elsewhere in this text.

Additionally PDT (photodynamic therapy) protocols can be applied using fluids like Methylen Blue or Toluidin Blue, which are applied into the canal and the appropriate light is coupled into the light passing down into the canal. For Methylen Blue 670 nm with around 150 mW are required and 635 nm with ~100 mW for Toluidin Blue. The advantage over traditional PDT procedures is the simultaneous delivery of Er:YAG/Er:YSGG laser energy to agitate the PDT fluid by laser energy, rapidly induce steam bubbles, adjacent fluid motion and heat the PDT fluid. This allows a much more intense contact of the fluids with the bacteria and debris.

Further it is helpful to know whether the cleaning procedure was successful by detecting remaining bacteria in the canals as described in this text with the example of root canal cleaning.

Of course this is not the only application for this cleaning technology. Many biotechnology procedures/bioreactors are endangered by bacteria, algae and debris deposition in small canals which can be cleaned with the proposed procedure and device.

And of course larger canals exceeding 1 mm diameter can be cleaned with this procedure as well then however requiring more laser pulse energy and multiple cleaning fibers positioned e.g. in an array or ring structure Required pulse energies are then in the order of n*0.1-50 mJ, where n is the number of single cleaning fibers.

In case of cleaning longer canals the terminal fiber introduced in the canal must have a better transmission than OH reduced silica. In that case sapphire is the ideal candidate material.

BRIEF DESCRIPTION OF THE DRAWINGS

The present invention can be better understood and its advantages appreciated by those skilled in the art by referencing to the accompanying drawings. Although the drawings illustrate certain details of certain embodiments, the invention disclosed herein is not limited to only the embodiments so illustrated.

DETAILED DESCRIPTION OF THE INVENTION

In the following, the invention will be explained on the basis of the cleaning of a canal, such canal being a root canal, however, without limiting the invention. Rather, the teaching according to the invention can be applied in all cases where particularly canals with small diameters are to be cleaned and/or closed as is for example the case with medical instruments, as explained in the introduction.

In case of a traditional root canal treatment, the pulp chamber is opened, the pulp tissue removed and the root canals are enlarged with mechanical files until a conical shape of the root canal is achieved. The canal is manually flushed with cleaning fluids via syringes.

Then the canal is filled with a sealer and conical gutta-percha points are plugged and condensed into the canal to achieve a dense root canal filling.

For this procedure canal enlargement is necessary to create a conical shape of the canal consistent with the conical shape of the Gutta-percha points filling the canal. The material loss weakens the tooth; the procedure is time consuming, bears the danger of over-instrumentation and file fracture. The success rate ranges from below 70% to 95% depending on who is doing the treatment.

An easier, less time consuming and technique sensitive procedure could help to raise the average success rate and increase the comfort for the patient.

A procedure without enlarging the root canal would avoid above mentioned disadvantages. However it creates new challenges. Not enlarging the canal results in irregular shaped root canals like a cave. Therefore traditional root canal cleaning and filling is not possible, because conically shaped Guttapercha points cannot be inserted in such an unshaped root canal. A new filling technology is required.

Laser assisted root canal procedures use steam bubbles generated by laser energy to cleanse root canals which are already enlarged with mechanical files to a conical shape typically to size #40 or more. The steam bubble expansion and contraction causes water motion in the vicinity of the bubbles, which then cleanse the root canal walls.

Fotona, Biolase and KaVo sell or have sold dental laser systems which can be used for such an endodontic treatment. These lasers offer a wide range of dental indications up to drilling of cavities. The pulse repetition rate of these devices is typically limited to ~50 Hz and they offer pulse energies up to 1 J, which is necessary for cavity preparation. For endodontic treatment pulse energy below 50 mJ is sufficient in combination with 50 Hz or less pulse repetition rate (*Thermal and acoustic problems on root canal treatment with different lasers,* T. Ertl, H. Benthin, G. Müller, *SPIE Vol.* 2327 *Medical Applications of Lasers* 11(1994); *Application of lasers in endodontics,* T. Ertl, H. Benthin, B. Majaron, G. Müller, *SPIE Vol* 3192 *Medical Applications of Lasers in Dermatology, Ophtalmology, Dentistry and Endoscopy* (1997)) and the use of conical shape fiber tips (*Canal Enlargement by Er:YAG Laser Using a Cone-Shaped Irradiation Tip,* S. Shoji, H. Hariu, H. Horiuchi, *J ENDONTICS VOL.* 26, No. 8. AUGUST 2000; 454-458).

These traditional flash lamp pumped Er:YAG/YSGG laser have an energy conversion efficiency of ~3% resulting in a large power supply and a bulky device with fluid cooling. This leads to a high price and thus very limited number of users.

Additionally these lasers are class 4 devices, the regulatory environment needs some efforts in a dental practice to comply with. A laser safety area must be declared and protected, a laser safety officer must be trained and nominated and DDS, assistant and patient need to wear eye protection goggles.

The actual laser assisted endodontic root canal procedure uses pulse energies in the range 5-30 mJ, which is above the ablation threshold of dentin. Therefore generating a wrong pathway (via falsa) is possible, when protruding the laser fiber into the root canal.

In a protocol provided by DiVito (*Effectiveness of the Erbium:YAG laser and new design radial and stripped tips in removing the smear layer after root canal instrumentation,* E. DiVito, O. A. Peters, G. Olivi, *Lasers Med Sci* (2012) 27:273-280) the laser applicator is placed in the pulp chamber and not protruded into the root canals. Even without the need for protruding the laser applicator into the root canal the procedure requires pretreatment of the root canals to size #25 or #30. The laser energy generates fluid movement in the pulp chamber, which extends into the root canals partially. In favor of the method no fiber must be protruded into the canal. However disadvantages are inconsistent results, depending on the canal geometry and splashing of corrosive cleaning fluids out of the pulp chamber even out of the mouth of the patient can be observed due to relative high pulse energies of 25-30 mJ.

Recent technology improvement enabled the design of diode pumped Er:YAG/YSGG lasers.

A diode pumped Er:YAG/Er:YSGG laser developed specifically for endodontic treatment offers a smaller device and more economical solution. This laser system is based on laser system developed by Pantec. (WO 2010/145802 A1, Bragangna, Heinrich, Pantec Biosolutions AG) Main reason is an improved efficiency of the conversion of electrical energy into light energy. This allows using a much smaller power supply and reducing the cooling efforts.

A higher pulse repetition rate (up to 2000 Hz compared to 50 Hz) allows decreasing the pulse energy below the ablation threshold of dentin. This is important, because it avoids the formation of a "via falsa" (penetrating the root canal wall into the periodontium), which is a significant complication in endodontic treatment.

Totally unexpected, pulse energies in the range of 0.8-4 mJ in combination with pulse repetition rates between 50 Hz and 2000 Hz preferably 50 Hz-800 Hz allow in combination with effective cleaning fluids efficient cleaning of root canals. The low pulse energy avoids splashing of the cleaning fluids, minimizes the vibration of the tooth during treatment and avoids a root canal wall perforation by the laser fiber during treatment, because the laser energy density is below the ablation threshold of dentin.

The canal treatment as a root canal treatment with the device disclosed according to the invention starts like the traditional procedure with opening the pulp chamber, removing the pulp tissue in the pulp chamber, searching for the canal entrances and slightly enlarging the entrances, followed by path finding with file size up to size #25 which created a pathway with at least 250 µm diameter at the apex and more diameter more coronal, which is necessary to protrude a laser fiber with same or smaller diameter close to the apex.

No further canal enlargement is required. This saves significant working time and increases the patient comfort The pulp chamber and the root canals are filled with cleaning fluid either manually with a syringe or automatically from fluid containers of the device and the laser fiber is inserted in to the root canal until 1 mm before the apex.

The laser radiation in a wavelength range 2.69-2.94 µm is strongly absorbed by fluids containing water and creates steam bubbles by vaporization in the fluid and causes hydrodynamic motion of the water in the root canal. This fluid motion cleanses the canal. The laser is activated and the laser fiber is moved up and down the root canal. Cleaning consists of removing vital and non-vital pulp tissue, bacteria and pus as well as opening the dentinal tubules. The main cleaning area is ~1-2 mm around the fiber tip and some less efficient "far distance" cleaning effects in the whole root canal, mainly caused by resonance phenomena as interaction between the root canal geometry and acoustic waves caused by steam bubble formation and collapse.

After cleaning, the canal with one fluid the canal is dried either conventionally with paper points or with laser energy (or both combined) to remove the cleaning fluid from the canal. Additionally compressed air can be used exiting the applicator supporting the drying process. Then optionally further cleaning fluids are filled into the root canals sequentially (Manually with syringes or automatically with the device) and the treatment is repeated. Finally the canal is dried again.

Possible cleaning fluids can be water, NaOCl (3-10%), EDTA (10-17%), and/or $H_2O_2$ (3-30%) or mixtures thereof.

Verdaasdonk et al. (WO 2013/049832 A2, Biolase inc., Netchitailo V., Boutoussov, D. Verdaasdonk, R. M. et al. Pressure wave root canal cleaning system) report on cleaning improvement with laser energies, typically larger than 5 mJ per pulse by adding gas bubbles to the cleaning fluid.

In contrary to Verdaasdonk's, disclosure cleaning with low pulse energies in the proposed range is less efficient, if the fluid contains gas bubbles before treatment. Best results are obtained with fluids without addition of gas bubbles or even degassed fluids.

To decide, whether a root canal is clean and dry enough and free of bacteria, a cleanliness check of the root canal can be done. Spectroscopic/fluorescent methods can be used guiding illumination/excitation light in the laser fiber into the root canal and collecting remitted light from the bacteria, debris and canal wall with same fiber. This can be done simultaneously to the laser cleaning. Bacteria emit fluorescence signatures in the visible wavelength range (especially 570 nm-650 nm) when excited with UV light (e.g. 405 nm) or in the near infrared range (e.g. 750-880 nm), when excited with red light 600-700 nm. Excitation in the visible range is preferable, because auto-fluorescence of dentin has a strong emission in the green spectral area around 530 nm.

Alternatively electrical impedance spectroscopy can be applied for canal diagnostics.

In case bacteria remain after cleaning in the root canal bacteria can be reduced by a specific temperature treatment using high repetition rate laser energy or/and a PDT procedure can be added to the treatment.

A pre-requisite for thermal killing of bacteria is a strong absorption of the laser radiation at the root canal surface. Diode lasers with emission wavelength between 750 nm and 980 nm used today for this purpose do not have a strong absorption in dentin, therefore are not ideal in part even dangerous, since the temperature rise in the periodontium and inside the root canal are nearly equal.

2.69-2.94 µm wavelength e.g. of the proposed diode pumped Er:YAG laser device is much better adapted to the task.

Therefore, low power Er:YAG laser radiation in the order of 0.5 W with 200-800 Hz pulse repetition rate is fully sufficient to reach local peak temperatures on the root canal wall well above 100° C. for killing bacteria and keeping the periodontal temperatures well below critical 43° C.

For PDT various protocols are available (e.g. Helbo, Dentofex, Wilson). For this treatment fluids like Methylen Blue or Toluidin Blue are applied into the root canal and the appropriate light is coupled into the light pass down into the root canal. For Methylen Blue 670 nm with around 150 mW are required and 635 nm with ~100 mW for Toluidin Blue. The advantage over traditional PDT procedures is the simultaneous delivery of Er:YAG/Er:YSGG laser energy to agitate the PDT fluid by laser energy, rapidly inducing steam bubbles, causing adjacent fluid motion, and heating the PDT fluid. This allows a much more intense contact of the fluids with the bacteria and increases the penetration depth into the dentinal tubules compared to PDT without agitation or agitation with ultrasound.

Filling not enlarged canals 10 as root canals requires a new approach capable of covering irregular root canal space without voids. This is possible with a low viscosity obturation material. The risk is however a penetration of the filling material over the apex.

An apical "plug" placed in the apical region before filling the canal with the low viscosity material can prevent this. Conventional solutions for placing an apical plug are disclosed already (e.g. US2009/0220909 A1 Müller, Mannschedel, Coltene/Whaledent) but require however a canal preparation according to ISO and cannot be applied to irregular canals. Further they do not disclose the use of a laser system to place the plug.

Figure 1:
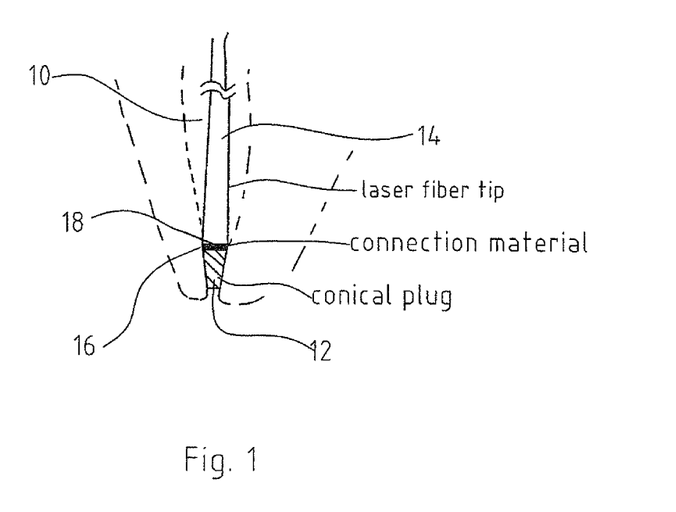
FIG. 1 depicts a diagram of a light guide with removable plug.

In case of a small apex with a diameter in the order of laser fiber (250-350 µm) a plug 12 is attached axially to the laser fiber 14 (FIG. 1). Optional a connection material 16 between the fiber tip 18 and the plug 12 may improve the adhesion between plug material and the fiber tip 18.

The plug material may be pre-heated before insertion in an external furnace actually used to pre-heat Thermafil obturators.

The plug material may be covered additionally with a sealer prior to insertion in the root canal 10. The sealer may be composed as disclosed in US2014/0017636 A1 Berger et al., Dentsply intl. inc.

The laser fiber 14 with the plug 12 is protruded in the root canal 10 and pushed with slight pressure in position. At appropriate working length (length to apex—1 mm) the laser is activated and the plug 12 or the connection material 16 begins to melt at the connection to the laser fiber 14. The plug 12 can be slightly vertically condensed with the laser fiber 14. That will hold the plug 12 in position while removing the laser fiber 14. In the next step the low viscosity material is filled into the canal. This material can be e.g. a root canal filling material as disclosed in US 2014/0335475 A1 Berger el al., Dentsply intl. Inc.

To improve the coverage of the root canal wall in recesses and not directly accessible areas the low viscosity filling material can be subjected to laser radiation, which is absorbed by the material and create steam bubbles, which accelerate the material against the root canal wall. Finally a material with same or higher viscosity (e.g. according to US 2014/0335475 A1) is filled into the canal to obturate the remaining canal volume. Lateral and/or vertical condensation may be applied.

Requirements for the plug material:
Bio-compatible
Hardness lower than dentin (relevant in case of re-treatment), gutta-percha is an option.

In case of a direct connection of the gutta-percha to the laser fiber 14 the gutta-percha formulation must have a stable connection to the laser fiber 14 at storage and during insertion into the canal 10 at room temperatures and must melt in between 50° C. and 200° C. Gutta-percha has an absorption coefficient high enough to deposit enough energy in a few $10^{th}$ of micrometers, which ensures a very local heating of the interface to the laser fiber.

In case a connection material is used the connection material 16 must melt in between 45° C. and 200° C. and attach sufficiently to the laser fiber 14 and the plug material. The absorption coefficient at the laser wavelength must be high enough to deposit sufficient energy in a few $10^{th}$ of micrometers to melt the connection material with a power of less than 2 W, preferably below 100 mW within 1-3 seconds. The material melts between 45° C. and 200° C., which insures shelf stability and keeps the temperatures in the apical region low enough during the heat application.

Alternatively the gutta-percha plug may be attached to an applicator which is heated electrically. A tiny SMD resistor (EIA01005, 0.2×0.2×0.4 mm) or semiconductor material at the tip of a plastic applicator feeded by 2 copper wires with less than 250 µm total diameter can be used.

In case of a wide apex 20 much wider than the fiber diameter e.g. 0.5-1 mm the above described approach would fail.

For such a situation a material is needed that can expand the volume "on demand" (like popcorn or polyurethane foam). The base material could be attached again to the laser fiber 14 protruded in position at the apex 20 and then the expansion is initiated by either laser energy converted to heat by absorption or UV light, but with a plug 112 comprising an expandable material 114. The plug material 114 must expand at temperatures lower than the melting temperature of the connection material. After expansion of the plug material 114 and after some second of cooling to allow the plug material 114 to get harder, the laser power is increased for a short time duration e.g. 0.5-2 seconds to finally melt the connection material and remove the fiber tip 14 from the canal 10 without the danger of displacing the plug 112 from its apical position during removal.

Ideally the expansion of the plug material 114 is directed towards the canal wall. To achieve this, the expandable material must be placed on the side of a volume scattering material attached to the fiber tip 18 with a connection material. After expansion this volume scattering material 114 will remain in the canal 16 as part of the plug 112. To separate the plug from the fiber tip, the connection material is heated with Er:YAG laser radiation. In this case the connection material must be transparent for radiation in the visible range, which is scattered by volume scattering part 120 of the plug 112 into the expandable plug material 114 to heat the expandable plug material 114.

The plug material can be a dental composite material. The connection material can be a translucent (in the visible wavelength range) resin softening at less than 200° C.

Figure 2:
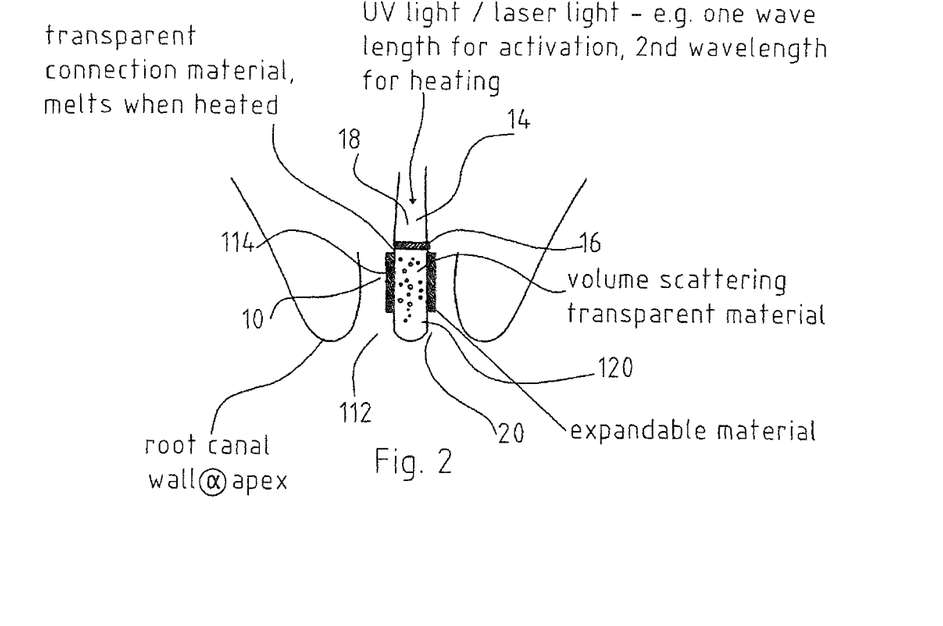
FIG. 2 depicts a diagram of a light guide inserted into a canal with an expanding plug.
Figure 3:
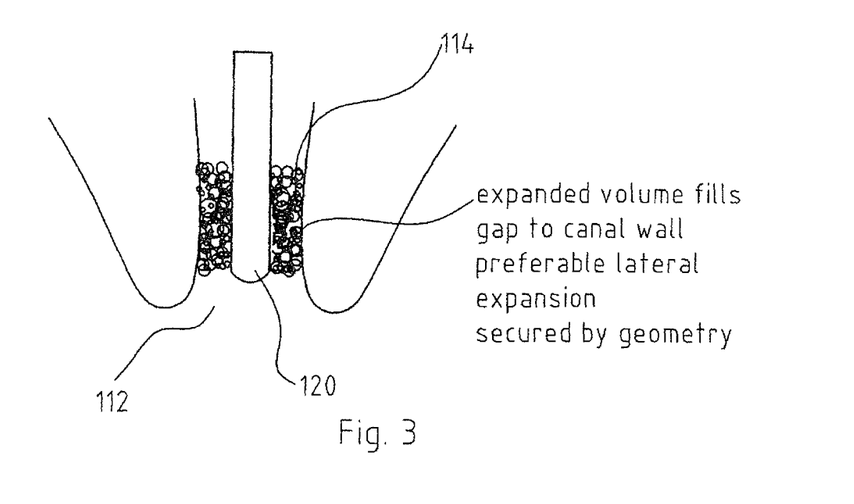
FIG. 3 depicts the arrangement according to FIG. 2 with an expanded plug.

The plug 112 with the middle part of the scattering material 120 and the expandable material 114 surrounding the core is depicted in FIGS. 2 and 3.

Another option is attaching a material component A as expandable plug material to the laser fiber and a second Material B is applied to the first material just before insertion into the root canal, which starts a reaction with volume expansion. The laser energy would then only be used to melt the connection of the plug material and the laser fiber, which has kept the plug material in the correct position before it fixes itself to root canal wall by expansion.

A material with an expansion factor of 3 can fill the gap between a #25 (250 µm diameter) plug and an apex diameter of #40 (400 µm diameter). An expansion factor of 7 can fill the gap to an apex diameter of #60 (600 µm).

In case a fiber tip with larger diameter can be inserted without canal enlargement, which is often the case in anterior teeth a material with an expansion factor of 3 could fill the gap between a #40 (400 µm diameter) plug and an apex diameter of #70 (700 µm diameter). An expansion factor of 7 could fill the gap in this example to an apex diameter of #100 (1000 µm).

Example for an expandable material: A mix of Natriumhydrogencarbonat (sodium bicarbonate)+guttapercha particles. When heat is applied via the optical fiber tip the following reaction $2NaHCO_3 \rightarrow Na_2CO_3 + CO_2\uparrow + H_2O$ releases $CO_2$ and forms a foam with the melted Guttapercha particles.

To keep the pH in physiological range an acid (e.g. Citric acid) may be added which will produce additional foam in a moist environment. Alternatively any biocompatible foaming agent in combination with Guttapercha including the disclosure in US2014/0017636 A1 and US 2014/0335475 A1 both Berger et al., Dentsply intl. inc. can be used.

Small sodium bicarbonate particles may be encapsulated in gutta-percha to create a closed bubble foam.

Examples of different kind of plugs, plug materials, connection materials, and expandable materials are specified in Table I.

source for apical plug heating and PDT is coupled into the light path with a dichroitic beam combiner. High power LEDs or laser diodes e.g. ADL-63V0ANP (Laser Components) may be used. The laser diode may be operated in parallel to the MID IR laser and is simultaneously transmitted to the handpiece. For fluorescence excitation (bacteria detection, canal cleanliness detection) cw or pulsed laser diodes in the range 350-700 nm are used.

TABLE I

| Plug Options | Plug material | Connection material (Plug to fiber) | Expandable material |
|---|---|---|---|
| Option 1 (Plug material directly fixed to fiber tip, no expansion) | Guttapercha, Thermafil | | |
| Option 2 (Plug material glued with connection material to fiber tip, no expansion) | Guttapercha, Thermafil | "Glue" melts between 50 and 200° C., biocompatible good adhesion to silica fiber and guttapercha | |
| Option 3 (Expandable plug material glued with connection material to fiber tip | expandable material | "Glue" melts between 80° C. and 200° C., biocompatible good adhesion to silica fiber and guttapercha | biocompatible material expands 3 to 7 times the original volume Expansion may start by heat (Temperature 50-70° C.) must be flexible like guttapercha |
| Option 4 (volume scattering plug base material glued with connection material to fiber tip, and covered with expandable material on the cone walls and apical) | Plug base material Optical properties like a Dental composite "Transpa" or "Enamel" semitranslucent and side scattering > 60% in visible spectral range must be flexible like guttapercha biocompatible | Glue melts between 80° C. and 200° C., biocompatible good adhesion to silica fiber and guttapercha | biocompatible material expands 3 to 7 times the original volume Expansion may start by heat (Temperature 50-70° C.) must be flexible like guttapercha |

Figure 4:
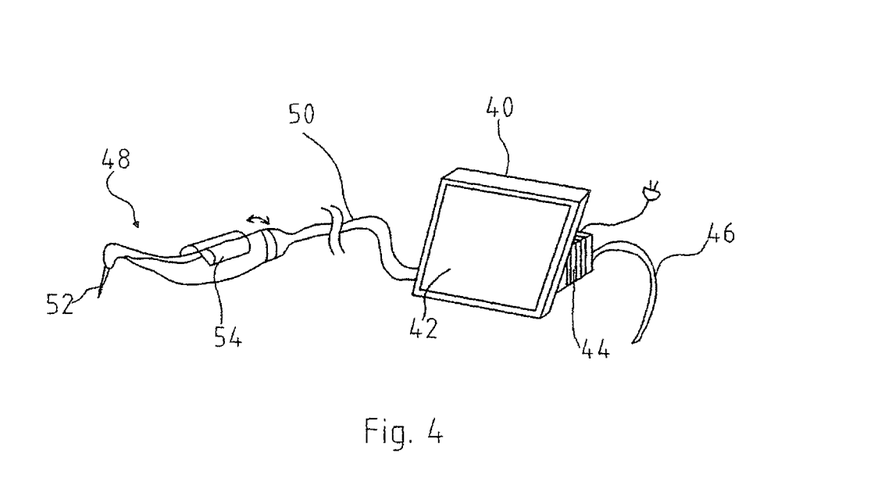
FIG. 4 depicts a diagram of the arrangement according to the invention.

A device according to the invention is shown in principle in FIG. 4. The device comprises a desktop device 40 with a touch screen 42 and a housing with integrated cooling elements 44. The housing is connected to the turbine connector of a dental unit 6 (connector 46) to have supply with water and compressed air.

The desktop housing is connected to a handpiece 48 with a delivery system 50.

The handpiece 48 is connected to the delivery system 50 via a rotation coupling. A fiber tip 52 can be connected to the handpiece and disposable containers 54 with cleaning fluid can be attached and removed from the handpiece. The housing is connected with the handpiece 48 via a connecting line 56.

The portable desktop device 40 comprises a laser as energy source. The laser radiation is transmitted with a delivery system together with water and compressed air and optionally cleaning fluids to the handpiece 48 with detachable fiber tip 52.

The energy source is a Diode pumped ER:YAG-(Wavelength 2.94 µm), Er:YSGG-Wavelength 2.78 µm) or CTE Laser (wavelength 2.69 µm). The pulse length is between 5-1000 µs, preferably 25-400 µs, most preferably 50-200 µs. The pulse energy is between 0.5-50 mJ, preferably 1-10 mJ at the distal end of the applicator. This requires around the double pulse energy at cavity exit. The average power is between 0.5-10 W preferably 1-3 W and the peak power is <600 W at cavity exit.

Further the device is equipped with light sources for aiming beam and apical plug heating and optional for bacteria detection and for PDT.

The aiming beam is coupled through the Er:YAG rod from the 100% reflection mirror side and the other light The device uses preferably air cooling for laser cavity and electronics.

Figure 6:
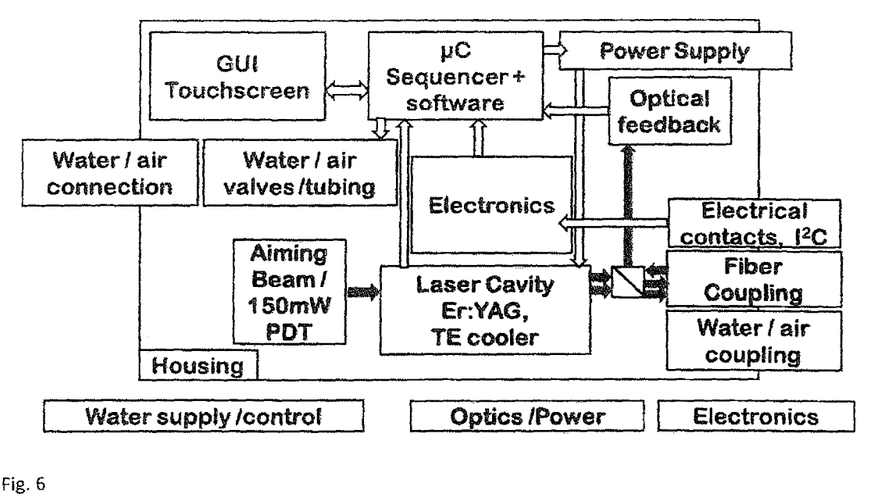
FIG. 6 depicts a block diagram of a laser system.

A schematic depiction of the laser system is shown in FIG. 6 which is self-explaining.

Especially, the invention is characterized by a diode pumped Er:YAG-/Er:YSGG/CTE:YAG laser providing a cleanliness check of the canal as root canal via the same optical fiber used for the canal cleaning with the following excitation/detection wavelength ranges for bacteria fluorescence detection.

a) Excitation 405-450 nm/detection 570-650 nm
b) Excitation 600-700 nm/detection 750-880 nm.

Further, the invention is characterized by a diode pumped Er:YAG-/Er:YSGG/CTE:YAG laser providing a cleanliness check of the canal as root canal via a metallization layer on the optical fiber tip used for the root canal cleaning using electrical impedance spectroscopy.

In addition, the invention is characterized by a diode pumped Er:YAG-/Er:YSGG/CTE:YAG laser providing energy (0.05 W-3 W with 200-800 Hz pulse repetition rate) into the canal as root canal via a fiber optic tip to heat the root canal inner surface via radiation absorption up to a 500 µm vicinity to temperatures lethal for bacteria reaching local peak temperatures on the root canal wall well above 100° C. and keeping the periodontal temperatures well below critical 43° C.

A further feature of the invention is a diode pumped Er:YAG-/Er:YSGG/CTE:YAG laser providing an additional light source emitting at 670 nm with around 80-200 mW and/or 635 nm with 50-150 mW to simultaneously initiate PDT with fluids like Methylen Blue or Toluidin Blue and agitate the PDT fluid by laser energy with rapidly induced steam bubbles and adjacent fluid motion and heat.

Water and compressed air are provided by plugging a dental turbine connector in a socket of the device. The device may have further exchangeable containers 54 for different cleaning fluids (sterile water, NaOCl, EDTA), if these containers 54 are not positioned directly at the handpiece 48. These cleaning fluid containers are pressurized by the compressed air of the dental chair provided by the dental turbine connector 46.

The fluid flow from these containers 54 to the handpiece 48 is controlled with electromagnetic valves operated via the μC (embedded micro-controller). Controlling the laser parameters and the sequencing of the cleaning fluids, laser assisted drying and compressed air allows a fully automated cleaning process canal by canal (TABLE II). The dentist needs just to press a start button and then move gently the fiber in the canal up and down until a ready sign appears (LED or Beep). Then the fiber 14 is inserted in the next canal and the procedure is repeated.

TABLE II

Optional: 30s $H_2O$, 100Hz, 1,8 mJ (Pre - cleansing, with low AVG power, create access for water in deeper canal sections)
30s $H_2O$, 400Hz, 1,8 mJ (Cleansing with 0,8W AVG power)
10s Rinse & dry canals with laser 800 Hz, 0,5 mJ, (laser drying is faster than with paper points)
30s 5,2% NaOCl 400Hz, 1,8 mJ (Dissolve pulp tissue)
10s Rinse & dry canals with laser 800 Hz, 0,5 mJ
60s 17% EDTA 50Hz, 3,5 mJ (every 6s for 1s laser treatment)
10s Rinse & dry canals with laser 800 Hz, 0,5 mJ Parameter Range
Min-max
[Preferred min-max]

TABLE III

| g | Time [s] | Pulse energy [mJ] | Pulse repetition rate [Hz] |
| --- | --- | --- | --- |
| Pre-cleaning | 10 - 120, | 0,25 - 30 | 50 - 500 |
| | [20 - 60] | [0,5 - 10] | [50 - 200] |
| Cleaning | 10 - 120, | 0,25 - 60 | 50 - 1000 |
| | [20 - 60] | [0,5 - 20] | [50 - 400] |
| Drying | 5 - 30, | 0,25 - 5 | 100 - 2000 |
| | [5 - 15] | [0,25 - 2] | [200 - 1000] |
| Cleaning with NaOCl | 10 - 120, | 0,25 - 60 | 50 - 1000 |
| | [20 - 60] | [0,5 - 20] | [50 - 400] |
| Cleaning with EDTA | 10 - 120, | 0,25 - 60 | 50 - 1000 |
| | [20 - 60] | [0,5 - 20] | [50 - 400] |

The laser parameters used when cleaning a canal are specified in TABLE III.

Mechanisms are provided to ensure that the laser can only operate, if the laser fiber 14 is placed in the root canal 10 to reduce laser safety risks.

When the fiber tip 18 is inserted into the root canal 10 the light received through the fiber 14 is far less compared to the fiber 14 being in ambient light. A detector in the laser system measures the light coming back from the fiber tip 18 and detects the absolute light level and the change in light level (first derivative). This detection can be done independently from any micro-controller or detection software. It is based on fixed wired hardware with a fail-safe design, which disables the laser system in case of a hardware fault in the detection unit.

The electronics further can detect the change of reflection of light emitted into the fiber delivery system (e.g. the aiming beam) when the refraction index difference changes while immersing the fiber tip 18 into the fluid contained in the root canal. The light of the aiming beam is amplitude modulated to differentiate the signal from the ambient light.

Figure 5:
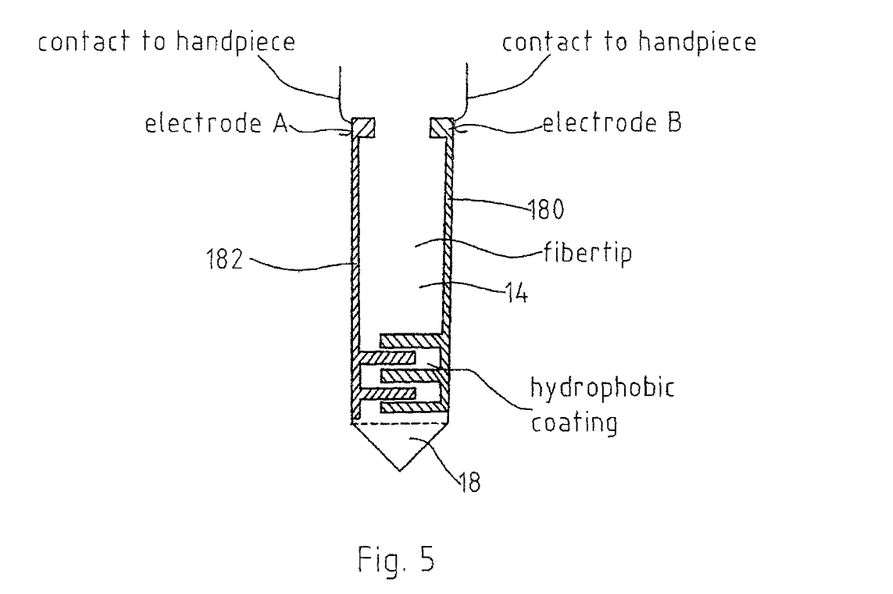
FIG. 5 depicts a diagram of an electrode arrangement of the light guide tip.

Another method to detect the fiber tip 18 position inside a root canal 10 is to metallize the surface of the fiber 14, inject a measurement current (AC) into the electrode(s) 180, 182 and measure the impedance change during insertion of the fiber into the root canal 10. The fiber 14 may be fully metallized as one electrode in combination with a counter electrode held by the patient or attached to the mouth of the patient (lip clip). A preferred solution is, however, a dual electrode concept, i.e. a first and a second electrode 180, 182, avoiding a counter electrode. Unambiguous connection is guaranteed by indexing the fiber tip.

Metallization layer may consist of a full coating of the optical fiber except the conical part of the fiber tip or may be a structured layer forming one or more electrodes on the same outer fiber surface.

A metallized tip configuration enables further "Canal is still wet" detection preferably with a dual electrode metallized fiber tip (see FIG. 5).

A wet canal has a significantly higher relative permittivity constant compared to a dry canal. $H_2O$: $\epsilon$ :80-90 and $\epsilon$ :3-30 compared to dentin $\epsilon$ :1-8 and $\epsilon$ :0.3-5. This can be utilized to determine the degree of humidity of the root canal. Measurement is done with a single frequency or multiple single frequencies or a sweep over a frequency band, which can be in the range 1 Hz to 10 GHz, preferably 1 kHz-2.4 GHz. A hydrophobic coating is applied in the area of the electrode to avoid direct not reversible wetting of the electrodes.

Using the canal humidity detection in combination with a laser based canal drying procedure, by applying laser energy with 0.1-1 W with 200-800 Hz pulse repetition rate allows a feedback controlled canal drying procedure.

Further impedance spectroscopy can be used for bacteria detection in the root canal 10 and length measurement during cleaning the canal 10. A special variant of impedance spectroscopy offered by NuMed (U.S. Pat. No. 9,119, 548B2) analyzing the harmonics generated by bacteria cell walls, can be integrated into the proposed cleaning device and allow bacteria detection in the root canal.

Using the metallized fiber 14, root canal length measurement with impedance measurements can be performed simultaneously with cleaning to indicate the correct position of the fiber tip 18 during treatment and not to exceed the apex 20.

To differentiate an upper jaw from a lower jaw treatment an inertial sensor e.g. is used (MEMs device e.g. Kionix KXTF9). This is important, since the fluid refill rate is different treating upper or lower jaw cases.

Further this inertial platform provides data for the movement direction of the fiber tip 18 (into- or out of the root canal 10). This is important to switch off the laser when pushing the fiber tip 18 into the root canal 10, in case an application requires an energy density above the ablation threshold.

Further the motion information provided by the motion sensor can be used to detect whether the dentist is continuously moving the fiber in the canal and remind the dentist with warning information, if he stops the movement during treatment and reduce or switch off the laser power.

Additionally the inertial platform data can be used to crosscheck with the fiber position data provided from the impedance based fiber position measurement.

The delivery system 50 connects the portable desktop device 40 with the handpiece 48 similar to a dental drill handpiece.

To avoid torque on the light guide the handpiece 48 is connected to the delivery system 50 with free rotation with low friction around the longitudinal axis.

The laser radiation is transported via a GeO, sapphire, $ZrF_4$ or any other light guide capable transmitting radiation (up to 50 mJ, up to 5 W Avg. power, 500 W peak power) in the wavelength range 2.69-2.94 µm and additionally 400 nm-1000 nm to the handpiece. The core diameter of the light guide fiber is between 150 and 600 µm, preferably 180-250 µm. The light guide end surfaces are protected against moisture and may be coated with an anti-reflective material.

Compressed air and water available at the dental unit of the dental chair, connected to the device is guided through the delivery system together with the light guide.

Optional further cleaning fluids from exchangeable containers plugged in the device can be transported in the delivery system to the handpiece.

Electrical wires provide data and power transport between handpiece and desktop unit. To keep the number of wires and connectors low, a SPI- or $I^2C$-bus system is used.

A bending protection insures that the fiber 14 is not bended beyond the allowed bending radius for oscillating bending.

The delivery system 50 is detachable from device in case of a need for repair and the handpiece 48 can be detached from the delivery system 50 routinely for cleaning/sterilization.

Figure 7:
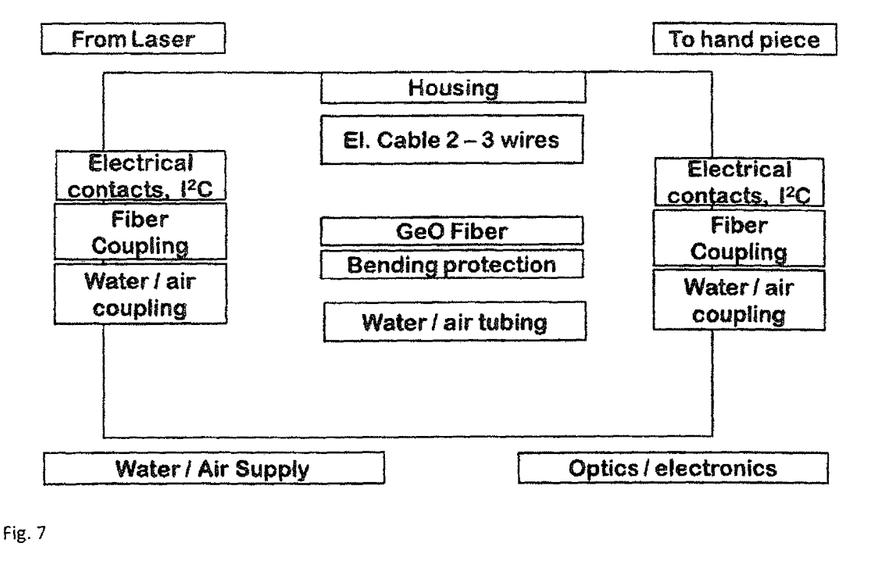
FIG. 7 depicts a block diagram of the delivery system.

FIG. 7 is a schematic depiction of the delivery system 50 which is self-explaining.

As an alternative to the placement of the motion sensor in the handpiece the sensor can be placed in the most distal part of the delivery system. This would avoid sterilization cycles to be applied to the sensor chip. Then however a rotation position detection between handpiece and delivery system must be added.

The handpiece 48 is connected with the delivery system 50 with a rotational coupling 58, which allows to deliver water (line 60) and pressurized air (line 62) to the handpiece 48. Air and water are delivered to the front section of the handpiece 48 and are applied towards the fiber 14 with nozzles 64. The laser radiation is supplied from the delivery system 50 with an optical fiber 66, via a protection window 68, a lens 70, and a deflection mirror 72 to the fiber 14. Fluid containers 54 are snapped on the handpiece 48. A motion sensor 74 is placed in the front section of the delivery system 50 and can detect in combination with a rotation encoder 76 the motion of the fiber tip 18 (see also FIG. 8).

Figure 8:
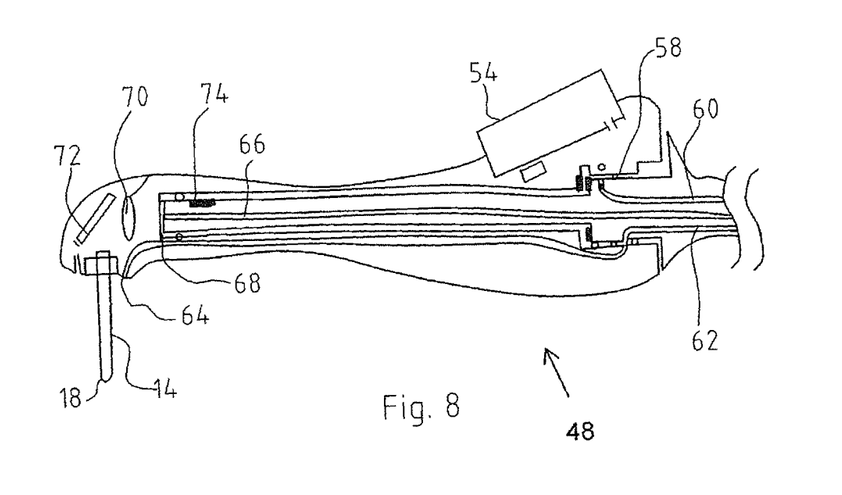
FIG. 8 depicts a diagram of a handpiece.

In the handheld applicator a removable, disposable fiber 14 can be plugged in under an angle in the order 70-130° to main direction of the handpiece 48. This fiber tip 18 is introduced into the root canal.

The handpiece 48 is comparable to a small dental handpiece, ideally contra-angle. The handpiece 48 is rotatable around longitudinal axis.

The laser beam deflection into attachable fiber 14 by ~90° is performed with the flat mirror 72 and a separate focusing element or a focusing mirror.

The disposable fiber 14 is connected to the handpiece 48 with a connector allowing unique positioning with an indexing connection to allow at least 2 electrical connections unambiguously being connected to contacts in the handpiece 48.

In a simple version of the handpiece 48 only water and air are available for the treatment directly out of the handpiece 48. Other cleaning fluids are applied manually with a syringe into the root canals 10.

Pressurized air and water may form a mist. 10-30 ml/min water and 5-10 l/min air are used to form the mist.

A fluid beam is directed towards the last ⅓ of fiber 14 with angle ca. 10-20° from fiber 14 longitudinal axis. The water speed at exit of the handpiece is larger than 0.6 m/s.

A Start/Stop button may be integrated in the handpiece.

Figure 9:
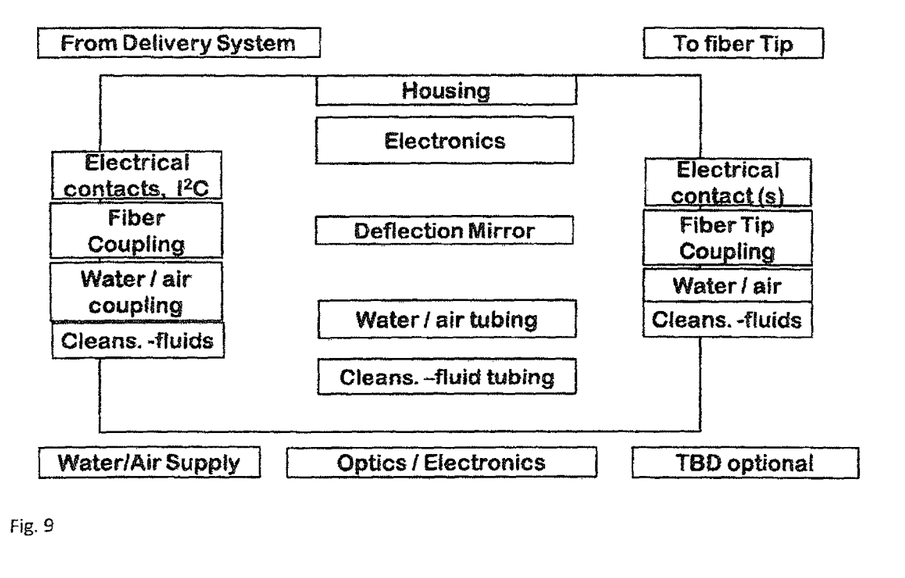
FIG. 9 depicts a schematic diagram of a handpiece.

A schematic depiction of the handpiece 48 with its components is shown in FIG. 9, which is self-explaining.

Figure 10:
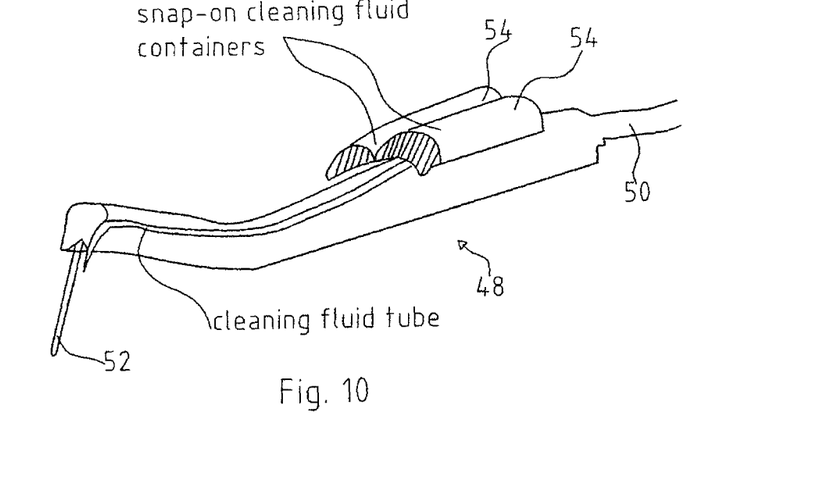
FIG. 10 depicts a diagram of a handpiece with fluid cartridges.
Figure 11:
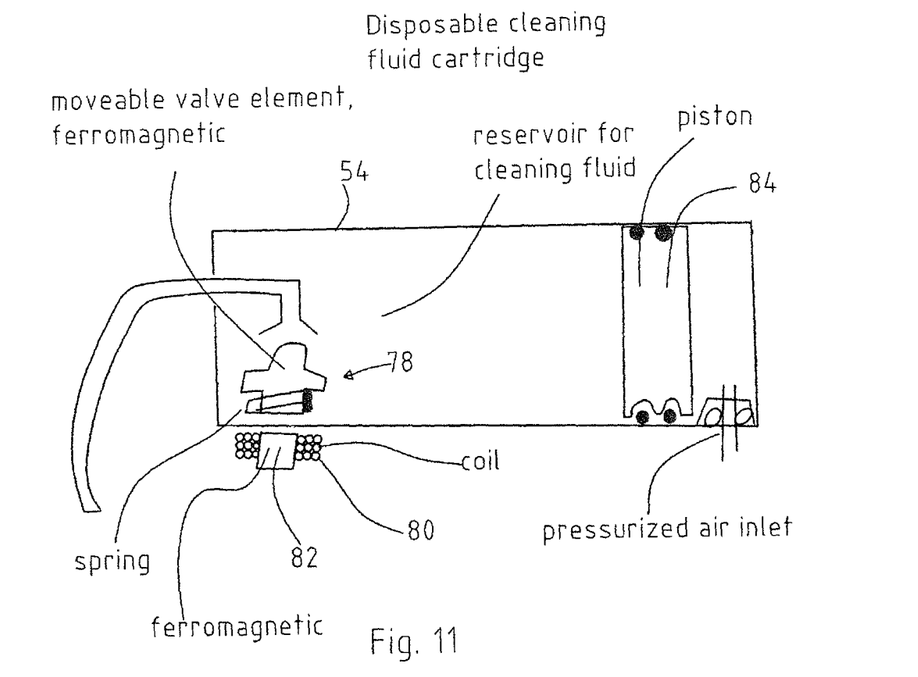
FIG. 11 depicts a diagram of a cartridge with valve.

In a variant of the handpiece 48 disposable fluid containers 54/(also called cartridges) for NaOCl and EDTA are directly attached to handpiece. The cartridge 54 has a fluid guidance close to the fiber 14 (see FIG. 10). A direct placement at the handpiece 48 is possible since the treatment requires only small amounts of fluid in the order of 1-2 ml per fluid. Main objective is to keep the partially corrosive fluids separate from the handpiece 48, delivery system 50 and desktop device 40. Further objective is to avoid dripping before and after usage. An inexpensive solution to achieve these objectives is the separation of an electromagnetic valve 78 into the excitation part with the magnetic coil 80 and a part of the ferromagnetic core 82 in the handpiece 48 and a ferromagnetic material as valve 78 opener as part of the exit valve in the disposable cartridge 54. The cartridge 54 is set under air pressure when placing the cartridge 54 in the handpiece 48. A flexible membrane or a piston 84 may separate the fluid from the air inlet. For more details, see FIG. 11.

Figure 12:
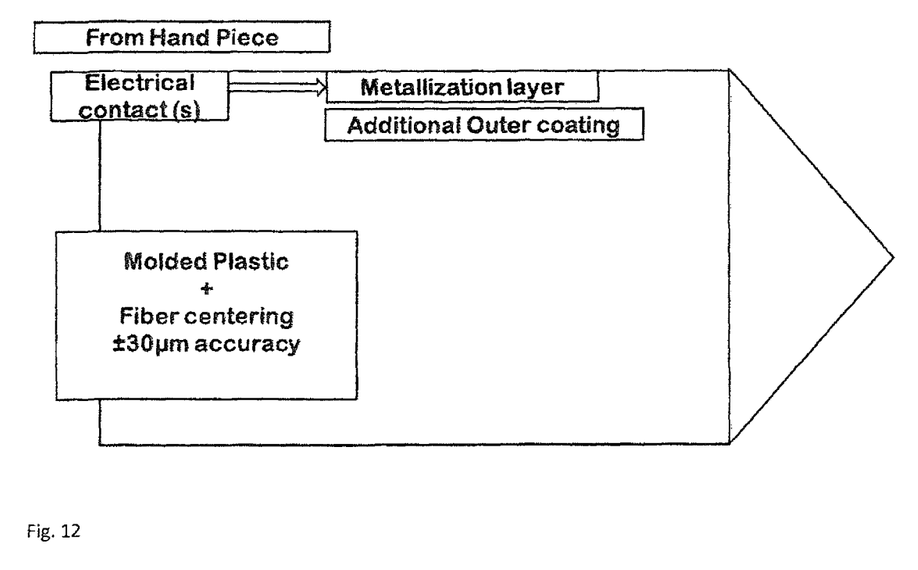
FIG. 12 depicts a diagram of a light guide.

The fiber material must allow the transmission of a wavelength range from 400 nm to 2.94 µm with reasonable loss and cost. OH reduced silica fibers are an acceptable compromise with ~50% attenuation over 5 cm length at 2.94 µm (including Fresnel reflection). The fiber 14 is a disposable surviving 3-4 root canals with moderate degradation. The end 18 of the fiber 14 is conically shaped without protection layer or metallization. Alternatively the fiber 14 can be hemispherical. The fiber 14 has an outer diameter of 200-300 µm and a core diameter of 180-240 µm. The length of the fiber 14 is between 30-40 mm. A molded plastic part connects the fiber 14 with the handpiece. The fiber 14 may have an additional coating to improve fracture resistance and may have a surface metallization to allow measuring the insertion length in the root canal, to determine the distance to the apex during treatment. The contact surfaces of the electrodes contact to connectors in the coupling to the handpiece 48. The coupling part to the handpieces 48 allows only 2 180° rotated positions to allow for unambiguous connection of the two electrodes. The electrodes 180, 182 may be covered with a hydrophobic layer. Further details of the fiber 14 with its tip can be learned from FIG. 12.

A software controls the laser parameters, air and water flow and in the extended handpiece 48 variant the flow of up to two additional cleaning fluids.

Sequencer programs are available for the following applications:

Cleaning/Drying
Bacteria detection
Thermal bacteria reduction
aPDT
Apical plug placement
Obturation support The Cleaning/drying program provides a sequence of cleaning and drying steps (see TABLE II).

The parameters can be programed individually and stored as "Preferred treatment programs".

Bacteria detection is a program to detect remaining bacteria and/or bacteria residuals in the root canal via fluorescence detection.

Thermal bacteria reduction is a program to heat the inner root canal surface locally in a clear defined way. Pulse repetition rates preferably between 100 and 2000 Hz are used in combination with low pulse energies (0.1-1 mJ) to generate locally temperatures on the inner root surface and within a few $100^{th}$ of μm in the root canal wall high enough to kill remaining bacteria. No fluids are used in this program. Fiber motion is monitored by the motion detector to avoid any risk of local over-heating.

The aPDT program combines the traditional aPDT sequence known e.g. from Helbo with the laser generated steam bubbles to create motion in the aPDT dye fluid to enhance the contact and fluid exchange along the root canal wall. Instead of a cleaning fluid container an aPDT dye is inserted in the handpiece. After the aPDT the Dye is washed out the root canal automatically by flushing with water with support of laser generated steam bubbles.

For an irregular, not shaped root canal 10 a different obturation strategy is required. To support such an obturation method the device offers the following programs:

The apical plug placement program is used in combination with a fiber with attached gutta-percha plug. With the laser heat is applied to partially melt the plug in apical position and detach it from the fiber tip.

The obturation support program is used to accelerate a low viscosity obturation material placed over the apical plug in the root canal against the root canal wall to enhance the dense coverage of the whole root canal wall with obturation material. For that purpose transient steam bubbles are generated in the root canal filling material. The applied heat can further reduce the viscosity during the application additionally enabling the obturation material to creep in any niche of the canal.

The invention provides an automated control of the laser parameters and the sequencing of the cleaning fluids, laser assisted drying and compressed air, which allows a fully automated cleaning process.

Although the invention has been explained above with the help of the cleaning of a root canal, the teaching according to the invention is, as was already explained, suitable for the cleaning of canals in which canals of smaller diameters as those of root canals are to be cleaned, particularly such canals which do not extend evenly in their longitudinal direction. With respect to this, reference is made to the introductory explanations.

The invention claimed is:

1. A method for the cleaning of a circumferentially closed canal using a light guide conducting a laser beam, comprising the steps of:
   providing the canal with a cleaning fluid;
   providing the light guide with the laser beam wherein the laser beam has a pulse energy below the ablation threshold of a canal wall material;
   monitoring movement and/or position of the light guide within the canal, and
   based on said monitoring step, interrupting an entry of the laser beam into the light guide when (i) a free end of the light guide is outside of the canal or (ii) there is no movement or (iii) movement is below a threshold value;
   wherein said interrupting is achieved by triggering a signal and/or turning off a laser radiation and/or reducing a laser radiation output and,
   wherein a positioning of the light guide is verified redundantly by measurement of:
   a) a value of radiation received inside the light guide, said radiation is derived from an area surrounding the light guide, and
   b) a value of a change of reflection of light emitted into a fiber delivery system when a refraction index difference changes while immersing a fiber tip of the light guide into said cleaning fluid contained in the canal, light of the laser beam is amplitude modulated to differentiate it from ambient light and
   c) a value of a change in impedance via an outer metallization of the light guide.

2. A method according to claim 1, wherein said monitoring is achieved by monitoring a position of the free end of the light guide within the canal.

3. A method according to claim 1, further comprising killing bacteria with photodynamic therapy protocols, wherein a photodynamic therapy fluid is applied into the canal and a corresponding light is simultaneously applied into the canal to agitate the photodynamic therapy fluid.

4. A method according to claim 3 wherein the photodynamic fluid is Methylen Blue or Toluidin Blue and wherein the corresponding light for Methylen Blue is about 670 nm, 150 mW and the corresponding light for Toluidin Blue is about 635 nm, 100 mW.

5. A method according to claim 1, further comprising:
   performing a cleanliness check of the canal via a fiber tip of the light guide using excitation/detection wavelength ranges for bacteria fluorescence detection including: (i) 405-450 nm for excitation and 570-650 nm for detection and/or (ii) 600-700 nm for excitation and 750-880 nm for detection.

6. A method according to claim 1, comprising performing the cleaning and the cleanliness check simultaneously.

7. A method according to claim 1, wherein the cleaning fluid comprises any combination of water, NaOCl (3-10%), EDTA (10-17%), and H2O2 (3-30%).

8. A method according to claim 1, wherein the canal is a root canal.

9. A method according to claim 8, wherein the laser beam is operable if a fiber tip of the light guide is inserted into the root canal, said insertion being detected based on using a detector to detect light coming back from the fiber tip, an ambient light level and a change in light level.

10. A method according to claim 8, further comprising measuring root canal length with a metalized light guide using impedance measurements wherein said measuring is performed simultaneously with said cleaning in order to indicate a position of the fiber tip during treatment such that a length of an apex of the root canal is not exceeded.

11. A method according to claim 8, wherein the cleaning fluid is applied manually into the root canal.

12. The method according to claim 1, wherein material present on an inside of the canal is removed through laser-induced hydrodynamic fluid movement.

13. The method according to claim 1, wherein movement of the light guide within the canal is further monitored with a motion sensor.

* * * * *